US006896894B2

(12) United States Patent
Brody et al.

(10) Patent No.: US 6,896,894 B2
(45) Date of Patent: May 24, 2005

(54) PROTEINS STABILIZED WITH POLYSACCHARIDE GUMS

(75) Inventors: Richard S. Brody, Worthington, OH (US); Sreedhara Alavattam, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 363 days.

(21) Appl. No.: 10/012,667

(22) Filed: Oct. 30, 2001

(65) Prior Publication Data

US 2003/0103933 A1 Jun. 5, 2003

(51) Int. Cl.[7] ............................. A61F 2/02; A61K 47/36
(52) U.S. Cl. ...................... 424/425; 424/424; 514/777; 514/780; 514/782
(58) Field of Search ................................ 424/424, 425; 514/777, 780, 782

(56) References Cited

U.S. PATENT DOCUMENTS

| 5,128,143 A | * | 7/1992 | Baichwal et al. |
| 5,240,843 A | | 8/1993 | Gibson |
| 5,492,821 A | | 2/1996 | Callstrom |
| 5,554,386 A | | 9/1996 | Groman |
| 5,612,053 A | | 3/1997 | Baichwal |
| 5,736,625 A | | 4/1998 | Callstrom |
| 5,834,273 A | | 11/1998 | Futatsugi |
| 5,917,021 A | | 6/1999 | Lee |

FOREIGN PATENT DOCUMENTS

| EP | 0 123 291 | | 4/1984 |
| EP | 0 376 361 B2 | | 11/1989 |
| EP | 0 950 663 A1 | * | 7/1998 |

OTHER PUBLICATIONS

Elven K. Bauman, L.H. Goodson, J.R. Thomson; Stabilization of Serum Cholinesterase in Dried Starch Gel; Analytical Biochemistry 19; (1967); pp. 587–592.

Arakawa, T. et al., Factors Affecting Short–Term and Long–Term Stabilities of Proteins, Advanced Drug Delivery Reviews, 2001, pp. 307–326, vol. 46.

* cited by examiner

*Primary Examiner*—Carlos A. Azpuru
(74) *Attorney, Agent, or Firm*—Patricia A. Coburn

(57) ABSTRACT

Described are heat stable aqueous solutions or gels comprising a biologically effective amount of a protein and an effective stabilizing amount of a polysaccharide gum as well as heat stable solutions or gels suitable for use in an implantable drug delivery device at body temperature. Also disclosed are lyophilized compositions having biologically activity, where such lyophilized compositions are formed by lyophilizing the stabilized solutions or gels of the invention.

32 Claims, 2 Drawing Sheets

(2 of 2 Drawing Sheet(s) Filed in Color)

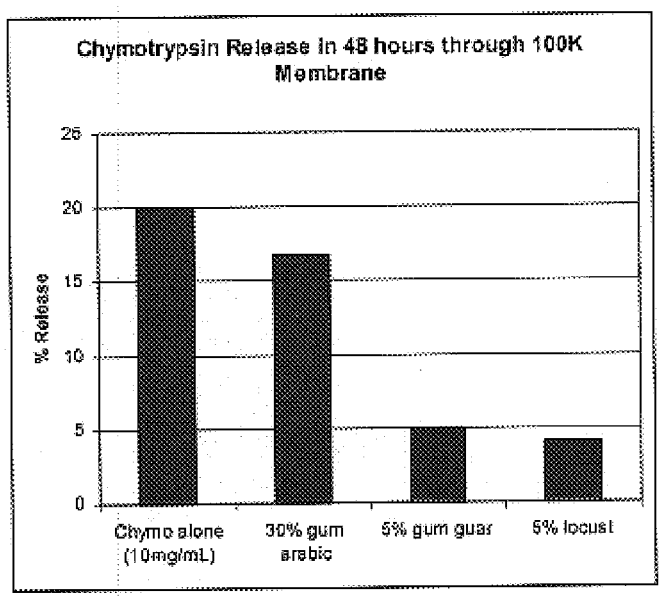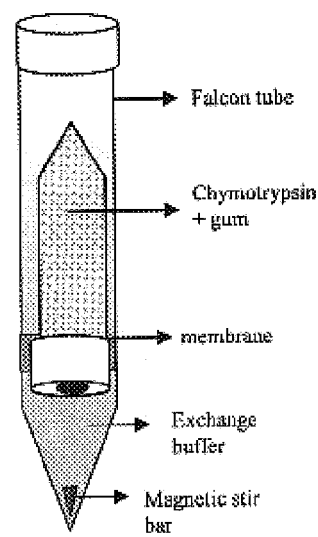
FIGURE 2: Chymotrypsin release through a 100K membrane using a 30% gum arabic, 5% gum guar or 5% locust bean gum solution.

PROTEINS STABILIZED WITH POLYSACCHARIDE GUMS

TECHNICAL FIELD

The present invention relates to a heat stable aqueous solution or gel comprising a biologically effective amount of a protein and an effective stabilizing amount of a polysaccharide gum as well as heat stable solutions or gels suitable for use in an implantable drug delivery device at body temperature. This invention also relates to lyophilized compositions having biological activity, where such lyophilized compositions are formed by lyophilizing the stabilized solutions or gels of the invention.

BACKGROUND OF THE INVENTION

The commercial market for recombinant protein biopharmaceuticals is expanding rapidly as various biotechnology and pharmaceutical companies develop and test biologically active proteins. The emerging field of proteomics will likely provide protein targets useful for drug development, thereby enabling the market for recombinant protein biopharmaceuticals to continue its expansion.

Currently, proteins are utilized in a variety of diagnostic and therapeutic applications. For example, one protein used in a diagnostic application is the enzyme glucose oxidase, which is used in glucose assays. The hormone insulin is an example of a protein utilized in therapeutic applications. However, proteins are particularly sensitive to certain environmental conditions and may not be stable at elevated temperatures, including physiological temperature of 37° C., in non-optimal aqueous solvent systems, or in organic solvent systems. Protein stability may also be affected by pH and buffer conditions and exposure to shear forces or other physical forces.

The stability of a protein refers to both its conformational stability, which is reflected in the protein's three-dimensional structure, and its chemical stability, which refers to the chemical composition of the protein's constituent amino acids. Protein instability can result in a marked decrease or complete loss of a protein's biological activity. Deleterious stresses such as organic solvents, extremes of pH, high temperatures, and/or dehydration (drying) can affect both the conformational and chemical stability of a protein. Chemical instability can result from (a) deamidation of the amino acids residues asparagine or glutamine, (b) oxidation of cysteine or methionine amino acid residues, or (c) cleavage at any of the peptide amide linkages of the protein. Examples of conformational instability include aggregation (fibrillation), precipitation, and subunit dissociation.

Because an inactive protein is useless, and in some cases deleterious, for most diagnostic and therapeutic applications, there is a need for a means by which proteins can be stabilized both in dry form and in solution. It is known in the art that proteins can be stabilized in solution by the addition of soluble excipients that stabilize the monomeric, correctly folded protein conformation. Disaccharides such as trehalose, sucrose, or lactose, and surface active agents such as phospholipids, Tween, and Triton are examples of excipients useful for stabilizing proteins. These stabilizers must be used in non-toxic levels because in the case of therapeutic proteins, the stabilizers are necessarily administered to the patient with the protein.

U.S. Pat. No. 5,834,273 issued to Futatsugi et al. on Nov. 10, 1998 provides a heat and protease resistant enzyme with improved storage stability. This enzyme is modified with a polysaccharide, polyamino acid, or synthetic polymer having a plurality of carboxyl groups by means of a crosslinking agent capable of binding both carboxyl groups and amino groups.

U.S. Pat. No. 5,736,625 issued to Callstrom et al. on Apr. 7, 1998 discloses a method for preparing water soluble, saccharide-linked protein polymer conjugates that stabilize the protein in a hostile environment. The claimed method includes covalently binding the polymer to the protein through at least three linkers, each linker having three or more hydroxyl groups. The protein is conjugated at lysines or arginines.

U.S. Pat. No. 5,691,154 issued to Callstrom et al. on Nov. 25, 1997 provides an enzyme linked immunoassay in which the enzyme is in the form of a water soluble polymer saccharide conjugate which is stable in hostile environments. The conjugate includes the enzyme which is linked to the polymer at multiple points through saccharide linker groups.

U.S. Pat. No. 5,612,053 issued to Baichwal et al. on Mar. 18, 1997 discloses a powder formulation which includes cohesive composites of particles containing a medicament and a controlled release carrier which includes one or more polysaccharide gums of natural origin.

U.S. Pat. No. 5,492,821 issued to Callstrom et al. on Feb. 20, 1996 discloses water soluble protein polymer conjugates in which proteins linked to an acrylic polymer at multiple points by means of saccharide linker groups. These conjugates are also stable in hostile environments.

U.S. Pat. No. 5,128,143 issued to Baichwal et al. on Jul. 7, 1992 provides a slow release pharmaceutical excipient of an inert diluent and a hydrophilic material including xanthan gum and a galactomannan gum capable of cross-linking the xanthan gum in the presence of aqueous solutions.

Ispas-Szabo et al. demonstrated that the ability of starch tablets to swell and release low molecular weight drugs could be controlled by the degree that the starch was cross-linked. No data related to protein stabilization was presented. *Carbohydrate Research* 323, 163–175 (2000).

Artursson et al. demonstrated that proteins could be incorporated into polyacryl starch microparticles. One incorporated protein, the enzyme carbonic anhydrase, retained a low amount of activity at temperatures where the free protein had no activity (e.g., >70° C.). At lower temperatures (e.g., <65° C.), however, the free enzyme was more stable than the enzyme incorporated into the microparticles. *Journal of Pharmaceutical Sciences* 73, 1507–1513 (1984).

Gliko-Kabir et al. demonstrated that the swelling of lyophilized guar gum powder in gastric or intestinal buffer could be reduced from approximately 100 fold to approximately 5 fold if the guar was crosslinked with glutaraldehyde. No data concerning protein stabilization was presented. *Pharmaceutical Research* 15, 1019–1025 (1998).

Bauman et. al. demonstrated that carrageenan gum stabilized the enzyme cholinesterase against heat when the enzyme was dried on a urethane foam sheet with 8% starch. *Analytical Biochemistry* 19, 587–592, (1967).

Many of the methods that are known to stabilize proteins, require that the protein be covalently attached to a solid support or covalently substituted with a stabilizing molecule. Covalent modification is not always practical for proteins in solutions, thus there is a need for a protein stabilization system that does not require covalent modification of the protein.

The typical method of administering therapeutic proteins to a patient or test subject is by means of needle-based injections. Currently, many pharmaceutical and drug delivery companies are seeking to develop alternative systems for the delivery of therapeutic proteins. These alternative systems are expected to require fewer dosings and to allow for more effective control over the rate of protein release in the body.

One alternative drug delivery system known in the art includes the formulation of the protein in a biodegradable polymer matrix. The polymer (e.g., poly(lactic-co-glycolic acid)) can be formulated as an injectable or respirable microparticle. Alternately, the protein can be formulated in a temperature sensitive polymer that is liquid at room temperature but solidifies at 37° C. after injection into a patient. In both cases, the polymer systems are developed for sustained release of protein over time; however, the stability of the protein during the release period is difficult to maintain and generally less than 50% of the total protein load can be delivered. Additionally, the delivery of the protein is not uniform, but rather occurs with a rapid initial burst which is followed by a much slower rate of sustained protein release.

A second type of known delivery system includes an implanted pump such as an osmotic pump. In this system, a suspension of protein in a water miscible organic solvent is continuously delivered to the patient or test subject through an orifice in the osmotic pump implant. However, use of this system may prove problematic because it is often difficult to suspend a high protein load in the organic solvent, and only some proteins are stable to prolonged incubation under the required non-aqueous or mixed organic-aqueous conditions.

Thus, given the current state of the art, there is a need for compositions and methods that effectively stabilize a variety of proteins in various chemical and physical environments, and that are compatible with a variety of drug delivery systems.

SUMMARY OF THE INVENTION

The present invention is directed to stable aqueous solutions of biologically active proteins wherein the protein solutions are stabilized by high molecular weight polysaccharide gums. The stable protein solutions may be used in drug delivery systems and are protected against stresses such as high temperatures, organic solvents, extremes of pH, drying, freezing, and agitation. Preferably, in the solutions of the invention, the polysaccharide gums are not bound to the protein.

According to a preferred embodiment, the aqueous solutions or gels of the invention include at least one biologically active protein, wherein the protein may be an enzyme, antibody, hormone, growth factor, or cytokine and at least one polysaccharide gum for stabilizing the protein, wherein the polysaccharide gum may be, for example, is gum arabic, guar gum, xanthan gum, locust bean gum, gum ghatti, gum karaya, tragacanth gum or a related polysaccharide Drug delivery systems compatible with the present invention include implanted subcutaneous delivery systems and intravenous drug delivery systems that can actively or passively deliver the biologically active proteins.

A preferred method for stabilizing a protein used in a drug delivery system includes the steps of providing a protein as an aqueous solution; adding at least one polysaccharide gum to the protein to form an aqueous solution or gel and adding the solution or the gel to a capsule, wherein the capsule further comprises a molecular membrane (FIG. 1). The capsule is fabricated from a biocompatible material, and contains the polysaccharide gum in a fixed volume for preventing the gum from swelling when exposed to an aqueous environment. The membrane of the capsule is fabricated from silica or a polymer and comprises pores of a size that make the membrane permeable to the protein but impermeable to the polysaccharide gum. Further advantages of the present invention will become apparent to those of ordinary skill in the art upon reading and understanding the following detailed description of the preferred embodiments.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2 is a tabular presentation of chymotrypsin release in 48 hrs. through a 100K membrane.

DETAILED DESCRIPTION OF THE INVENTION

Figure 1:
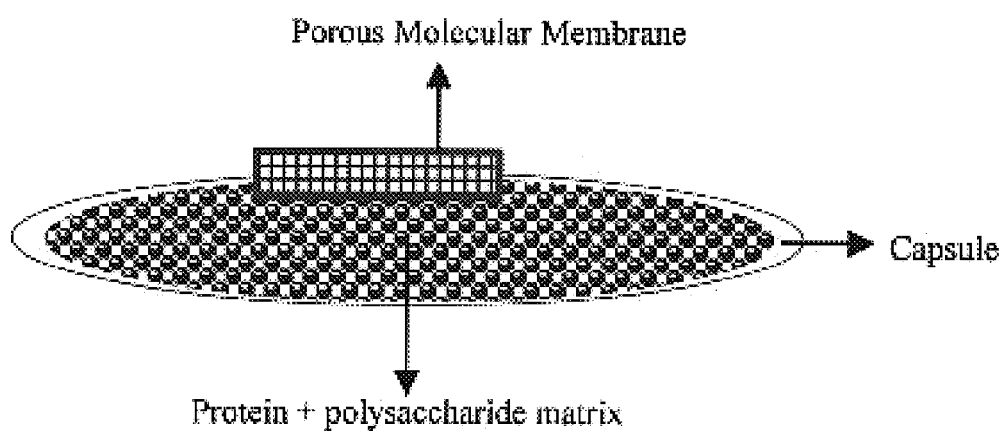
FIG. 1 is a schematic diagram of a capsule with a semi-permeable membrane.

The present invention is directed to a heat stable aqueous solution comprising a biologically effective amount of a protein and a stabilizing effective amount of a polysaccharide gum material. The invention is further directed to a heat stable aqueous solution comprising a biologically effective amount of a protein and a stabilizing effective amount of a polysaccharide gum material wherein said protein is selected from the group consisting of an enzyme, an antibody, a hormone, a growth factor, and a cytokine wherein said gum is selected from the group consisting of gum arabic, guar gum, xanthan gum, locust bean gum, gum karaya, gum ghatti, and tragacanth gum.

Another embodiment of the invention relates to a heat stable solution comprising a pharmaceutically effective amount of a protein and a stabilizing effective amount of a gum material wherein said stabilized solution is contained in an implantable drug delivery device.

A further embodiment of the invention is directed to a lyophilized composition having biological activity, wherein said lyophilized composition is formed by lyophilizing a heat stable solution or gel comprising a biologically effective amount of a protein and a stabilizing effective amount of a gum material.

As used herein the term "biologically active protein" includes proteins and polypeptides that are administered to patients as the active drug substance for prevention of or treatment of a disease or condition as well as proteins and polypeptides that are used for diagnostic purposes, such as enzymes used in diagnostic tests or in in vitro assays as well as proteins that are administered to a patient to prevent a disease such as a vaccine. Contemplated for use in the compositions of the invention are therapeutic proteins and polypeptides such as enzymes, e.g., glucocerebrosidase, adenosine deaminase; antibodies, e.g., Herceptin® (trastuzumab), Orthoclone OKT®3 (muromonab-CD3); hormones, e.g., insulin and human growth hormone (HGH); growth factors, e.g., fibroblast growth factor (FGF), nerve growth factor (NGF), human growth hormone releasing factor (HGHRF), and cytokines,e.g., leukemia inhibitory factor (LIF), granulocyte-colony stimulating factor (G-CSF), granulocytemacrophage-colony stimulating factor (GM-CSF), interleukin-6 (IL-6), interleukin-11 (IL-11), interleukin-9 (IL-9), oncostatin-M (OSM), and ciliary-neurotrophic factor (CNTF).

The term "pharmaceutically effective amount" refers to that amount of a therapeutic protein having a therapeutically relevant effect on a disease or condition to be treated. A therapeutically relevant effect relieves to some extent one or more symptoms of a disease or condition in a patient or returns to normal either partially or completely one or more physiological or biochemical parameters associated with or causative of the disease or condition. Specific details of the dosage of a particular active protein drug may be found in the drug labeling, i.e., the package insert (see 21 CFR § 201.56 & 201.57) approved by the United States Food and Drug Administration.

Polysaccharide gums are natural products extracted from various plants, trees and bacteria, such as *Cyamopsis tetragonolobus* (guar gum) and *Ceratonia siliqua* (locust bean or carob gum) and *Astragalus gummifer* (tragacanth) from plants of the Leguminosae family; gum arabic and tamarind gum from respectively the *Acacia senegal* tree and *Tamarindus indica* tree; xanthan gum from the bacterial genus *Xanthamonas campestrisgum* ghatti from *Anogeissus latifolia* and gum karaya from *Sterculia urens*. Many grades and forms of polysaccharide gums are commercially available.

The gum Arabic used in the solutions of the invention has a highly branched galactose core with linkages to other sugars and contains ~1% glycoprotein; the locust gum used herein has a mannan chain (1->4) with galactose substitued at the 6-position of ~20% of the mannose units; the guar gum used herein has a mannan chain (1->4) with galactose substitued at the 6-position of ~40% of the mannose units; and the xanthan gum used herein has a glucan (1->4) chain with trisaccharides substituted on every other glucose.

According to the preferred embodiment of the present invention, increasing concentrations of high molecular weight polysaccharide gums (i.e., greater than 200K) are utilized for effective protein stabilization. The polysaccharide gums described herein are more effective protein stabilizers than commonly used small molecule protein stabilizers such as monosaccharides, disaccharides, and detergents. High molecular weight, branched chain or substituted polysaccharides such as gum arabic, guar gum, xanthan gum, locust bean gum, tragacanth gum, gum karaya and gum ghatti are more effective protein stabilizers than linear chain polysaccharides such as cellulose, agarose, xylan, konjak, or chitosan. The polysaccharide gums used herein are generally used at the concentration of gum (% W/V) that is the upper limit of the solubility of the particular gum in aqueous solutions. The gums used herein will form either a viscous solution in water or will form a gel. In general, from about 0.5% to from about 35% weight to volume ("W/V") will be used depending on the particular polysaccharide. As used herein, the term "solution" refers to gels as well as to viscous solutions.

Polysaccharide gums are hydrogels that can absorb many times their weight of water. Therefore, it is preferable to restrict the tendency of the gums to swell in order to maintain the high polysaccharide concentrations that effectively stabilize proteins. The high gum concentration can be maintained by enclosing the gels in a capsule with a molecular membrane that is permeable to the protein but impermeable to the higher molecular weight gum. The capsules can be implanted in a patient or test subject for the controlled release of stabilized protein over extended periods. Over time, the protein is steadily released from the capsule thus, decreasing the concentration of protein inside the capsule while the concentration of the stabilizing gum within the capsule remains constant.

The present invention includes polysaccharide gums that are incorporated into drug delivery devices for the purposes of (i) stabilizing proteins and (ii) controlling the rate at which the proteins diffuse from the delivery device. The polysaccharide gums of the present invention stabilize native protein conformations, even at high protein concentrations. Thus, the delivery device can be loaded with a protein/gum composition that contains a high concentration of protein, or with a mixture in the solid form, thereby increasing the drug load of the device.

In various embodiments, the compositions of the present invention are utilized for the stabilization of proteins during membrane-controlled release from capsules or other devices implanted into a patient or test subject. In this case, the delivery device is designed to prevent the polysaccharide from swelling so that the stabilizing effects of high polysaccharide concentrations are maintained inside the capsule. Since it is unnecessary for the polysaccharide gums described herein to bind to proteins to effect protein stabilization, proteins can be released from the solution by diffusion. Additionally, the polymeric properties of polysaccharide gums provide an additional mechanism for stabilizing proteins by restricting a protein's molecular mobility.

In one embodiment of the present invention, high molecular weight polysaccharide gums are used to stabilize therapeutic proteins delivered by means of implanted drug delivery devices such as a capsule, wherein the capsule includes a molecular weight cut-off membrane with uniform pore size. The polysaccharide gum stabilizes the protein contained by the capsule and the release of the protein can be controlled by the membrane which is permeable to the therapeutic protein but impermeable to the higher molecular weight gum. This embodiment, therefore, would not necessarily be compatible with small molecular weight stabilizers that would diffuse out of the capsule faster than the protein. The membrane retains the polysaccharide gum in the capsule and the capsule prevents the gum from swelling and decreasing in concentration. The rate at which the protein diffuses from the capsule can be controlled by the viscosity of the gum as well as by the permeability of the membrane.

The physical state of the polysaccharide gums of the present invention depends on the conditions used to prepare the gum solutions. Viscosities can vary several fold for each gum depending on factors such as the mixing rate used to prepare the hydrated gum and whether the gum was heat treated or freeze-thawed. Manipulating the viscosity of the gums will permit the rate at which proteins are released from the gums to be controled as the rate of diffusion is inversely proportional to the solution viscosity.

The stabilized protein solutions of the invention may contain minor amounts (from about 0.5% to about 5.0% W/V) of auxiliaries and/or excipients, such as N-acetyl-dl-tryptophan, caprylate, acetate, citrate, glucose and electrolytes, such as the chlorides, phosphates and bicarbonates of sodium, potassium, calcium and magnesium. They can furthermore contain: acids, bases or buffer substances for adjusting the pH, salts, sugars or polyhydric alcohols for isotonicity and adjustment, preservatives, such as benzyl alcohol or chlorobutanol, and antioxidants, such as sulphites, acetylcysteine, Vitamin E or ascorbic acid.

Suitable tonicity adjustment agents may be, for instance, physiologically acceptable inorganic chlorides, e.g. sodium chloride; sugars such as dextrose; lactose; mannitol; sorbitol and the like. Preservatives suitable for physiological administration may be, for instance, esters of parahydroxybenzoic acid (e.g., methyl, ethyl, propyl and butyl esters, or mixtures of them), chlorocresol and the like.

The pH of the solution can be adjusted using a physiologically acceptable acid e.g. an inorganic mineral acid such as hydrochloric, hydrobromic, sulfuric, phosphoric, nitric and the like, or an organic acid such as acetic, succinic, tartaric, ascorbic, citric, glutamic, benzoic, methanesulphonic, ethanesulfonic and the like, or a physiologically acceptable base, such as sodium hydroxide, potassium hydroxide, calcium hydroxide, magnesium hydroxide and the like, an physiologically acceptable buffer solution, e.g., a chloride buffer, an acetate buffer, a phosphate buffer and the like.

In another embodiment of the present invention, the drug delivery device is a capsule that is filled with multiple layers of polysaccharide gums of varying viscosities. This capsule includes a molecular membrane capable of retaining the gum, but which is permeable to various therapeutic proteins. In this embodiment, a layer of viscous gum (e.g., guar gum) adjacent to the polymer membrane controls the rate of release of the protein by diffusion from the capsule, while a layer of less viscous gum (e.g., gum arabic) that has been formulated with the protein provides a stable reservoir of protein.

In still another embodiment, hollow fibers with specifically defined molecular weight cutoffs are filled with solutions or gels of gum and protein. Hollow fibers with controlled pore sizes are useful for rapidly dialyzing proteins. Preferably, the fibers are made of biocompatible materials that can be implanted in a patient or test subject. The fibers may be filled with solutions of protein formulated with guar gum or with locust gum. The gums control the rate of protein release as well as providing protein stabilization during release. Because the hollow fibers have a very large surface area to volume ratio, this approach is most useful for gum/protein gels with slow protein diffusion rates. A positive attribute of an implant that contains multiple hollow fibers is that all the therapeutic protein will not be in the same capsule, thereby lessening the possibility of a capsule failure, which might release a toxic dose of the protein.

An alternate embodiment of hollow fibers includes the steps of filling the hollow fibers with a gum arabic/protein solution and imbedding multiple fibers in a matrix of guar or locust gums. The guar or locust matrix is then enclosed in a dialysis membrane or a membrane enclosed capsule. This embodiment has many of the stabilization and diffusion properties of the multi-layered capsule approach, but in this case the main drug load is not in a single capsule and is, therefore, less vulnerable to a single capsule failure.

According to the present invention, a preferred method for stabilizing a therapeutic protein in a drug delivery system comprises the steps of (a) providing a protein as an aqueous solution; (b) adding a polysaccharide gum to the protein; and (c) adding the gum/protein solution or gel to a capsule that contains a molecular membrane. Alternatively, the protein/polysaccharide gum can be dried by lyophilization or spray drying and added to the capsule. In this method, the capsule is preferably fabricated from a biocompatible material and capable of containing the polysaccharide gum in a fixed volume to prevent the gum from swelling upon exposure to an aqueous environment. The capsules comprise a single large protein reservoir or may be comprised of a plurality of hollow fibers. The membrane is fabricated from silica or a polymer and has pore sizes, which permit the membrane to be permeable to the protein but impermeable to the higher molecular weight polysaccharide gum. The polysaccharide gum is selected based on its ability to both stabilize the protein and control the protein's rate of release. In this method, multiple gums and multiple layers of gums can be used in the capsule.

The following examples illustrate the effectiveness of the compositions and methods of the present invention in stabilizing proteins under different environmental conditions and in different model delivery systems.

EXAMPLE 1

A 1 mg/ml solution of chymotrypsin was made by dissolving 20 mgs of chymotrypsin in 20 mL of phosphate buffered saline (PBS, pH 7.4). Solutions of the gums containing chymotrypsin were made as follows: 1.87 ml of 1 mg/mL chymotrypsin solution in PBS was added to 0.83 g of gum arabic and homogenized to give a 33% solution. Similar procedure was repeated for 33% sorbitol. To 0.5 g of tragacanth gum, gum guar or xanthan gum, 2 ml of 1 mg/mL chymotrypsin in PBS was added and homogenized to give a 20% solution. To 0.625 g of gum karaya and gum ghatti, 1.875 mL of 1 mg/mL chymotrypsin in PBS was added and homogenized to give a 25% solution. Similarly, to 0.35 g of locust bean gum, 2.15 mL of 1 mg/mL chymotrypsin in PBS was added and homogenized to give a 14% solution. The pH of all the solutions, except 33% sorbitol, was adjusted to 7.4 using 1M NaOH. All the samples (33% gum arabic, 33% sorbitol, 20% tragacanth gum, 20% gum guar, 20% xanthan gum and 14% locust bean gum) were prepared in 50 mL centrifuge tubes and incubated at 60° C. for 7.5 min in a water bath. The samples were cooled on ice and diluted 20-fold in order to give a final concentration of 0.05 mg/mL chymotrypsin. Dilutions were performed by adding 31.73 mL PBS to the 33% gum solutions, 35.625 mL for the 25% gum solutions, 38 ml PBS for the 20% gum solutions and 40.85 mL PBS to the 14% gum solution. These solutions were homogenized before assaying them for chymotrypsin activity using N-benzoyl L-tyrosine ethyl ester as the enzyme substrate according to published literature (J. Biotech, 1994, v35, p9–18). The results are summarized in Table 1.

TABLE 1

The Effect of Polysaccharides on the Stability of the Enzyme Chymotrypsin Incubated at 60° C. for 7.5 Minutes

| Stabilizer | Concentration of Stabilizer (% w/v) | % Recovery 60° C. | % Recovery Room Temp. |
| --- | --- | --- | --- |
| None | — | 0% | 100% |
| Sorbitol | 33% | ~27% | ~90% |
| Gum Arabic | 33% | ~98% | ~100% |
| Locust Gum | 14% | ~85% | ~100% |
| Guar Gum | 20% | ~92% | ~100% |
| Xanthan Gum | 20% | ~50% | ~100% |
| Tragacanth gum | 20% | ~68% | ~100% |
| Gum Karaya | 25% | ~30% | ~75% |
| Gum Ghatti | 25% | ~30% | ~100% |

As shown in Table 1, in accelerated aging study performed at 60° C., gum arabic, guar gum, xanthan gum, locust bean gum and tragacanth gum all stabilized the activity of the enzyme chymotrypsin over 50%. Recoveries are significantly higher than those obtained by incubation with sorbitol, a monosaccharide shown in the literature to stabilize chymotrypsin. Other gums such as gum karaya and gum ghatti, stabilized chymotrypsin activity around 30%, Following the procedure of Example 1, other polysaccharides and two surfactants were tested. None of the materials listed in Table 2 were effective to stabilize aqueous solutions of chymotrypsin against elevated temperatures.

TABLE 2

Polysaccharides and Surfactants that
Do Not Stabilize Chymotrypsin at 60° C.

| Additive | Concentration of Sugar or Surfactant | Structure |
| --- | --- | --- |
| Cellulose | 25% | Linear β1,4 A-glucose chain |
| Agarose | 14% | Linear chain of galactose and anhydro-galactose |
| Beechwood Xylan | 50% | Linear xylose chain |
| Barley Beta Glucan | 17% | β1,3-glucan chain |
| Konjak Glucomannan | 25% | Linear chain of glucose + mannose |
| Chitosan | 17% | Linear chain of anhydro-N-acetyl glucosamine |
| Untreated Starch | 33% | Branched amylopectin + linear amylose |
| Dextran | 33% | α 1,6-anhydro-D-glucose chain |
| Tween 20 | 1% | Polyoxyethylene(20)sorbitan monolaurate |
| Tween 80 | 1% | Polyoxyethylene(20)sorbitan monooleate |

Following the procedures described in Example 1, the concentration of chymotrypsin in the solution was varied and the concentration of gum Arabic was held at 33% (w/v) in the solution. The results are summarized in Table 3.

TABLE 3

Stabilization of Increasing Concentrations
Of Chymotrypsin by Gum Arabic

| Gum Arabic Concentration (% w/v) | Chymotrypsin Concentration (mg/ml) | % Activity 7.5 Min., 60° C. |
| --- | --- | --- |
| 0 | 1.0 | 0 |
| 0 | 3.3 | 0 |
| 0 | 10. | 0 |
| 0 | 33. | 0 |
| 0 | 100 | 0 |
| 33% | 1 | 97 ± 17%[a] |
| 33% | 3.3 | 62 ± 6%[a] |
| 33% | 10 | 57 ± 5%[a] |
| 33% | 33 | 41%[b] |
| 33% | 100 | 53%[b] |

[a]Average result of two experiments
[b]Result of a single experiment

EXAMPLE 2

Gum arabic (33%)chymotrypsin solutions were prepared as described in Example 1, with the exception that PBS was made with 0.1% sodium azide. A solution containing 1 mg/ml chymotrypsin and no gum arabic was prepared as the control. Aliquots (2.5 ml) of the test and control solutions were added to 50 ml centrifuge tubes and these tubes were incubated at 37° C. for a period of time. The results are summarized in Table 4.

TABLE 4

Chymotrypsin Stabilization at 37° C. by 33% Gum Arabic

| Stabilizer | Time Weeks | % Activity |
| --- | --- | --- |
| Control (None) | 0 | 100 |
| Control | 1 | 15 |
| Control | 2 | 0 |
| Control | 4 | 0 |
| Gum Arabic | 1 | 130 |
| Gum Arabic | 2 | 80 |
| Gum Arabic | 4 | 82 |
| Gum Arabic | 8 | 58 |

As shown in Table 4, gum arabic was tested for its ability to stabilize chymotrypsin to long-term incubation at 37° C. in aqueous buffer, pH 7.4 (physiological conditions). The results shown in Table 4, indicate that gum arabic protects approximately 60% of the activity of chymotrypsin against incubation at 37° C. for eight weeks. In contrast, all the activity is lost over one week at 37° C. for chymotrypsin with no stabilizer.

It is important that the concentration of the gum stabilizer in the aqueous solution be high enough to effectively stabilize the protein. The stabilization of the particular protein is dependent on the concentration of polysaccharide gum in the solution. As shown in Table 5, the activity of chymotrypsin exposed to heat stress depends on the concentration of gum, with higher concentrations giving better stability.

TABLE 5

High Gum Concentrations are Required for Optimal Protein Stabilization

| Concentration (% W/V) Of Gum Arabic | % Activity Recovered 1 Week, 37° C. |
| --- | --- |
| None | 0 |
| 33 | 73 |
| 20 | 85 |
| 10 | 62 |
| 5 | 43 |
| 2.5 | 21 |
| 1.0 | 17 |

As indicated in Examples 1 and 2, chymotrypsin is stabilized by gum arabic, guar gum, xanthan gum, tragacanth, gum karaya, gum ghatti and locust gum. Gum arabic is an effective stabilizer at a concentration of about 1 to 33% (w/v), guar gum is effective at a concentration of about 2.5 to 20% (w/v), xanthan gum and tragacanth gum are effective at a concentrations of about 1.5 to 20% (w/v), gum karaya and gum ghatti are effective in the concentration range of 1 to 25% and locust gum is effective at a concentration of about 1 to 14% (w/v).

The polysaccharide gum stabilizers described herein, not only are able to stabilize proteins in solution but are also able to protect such proteins through conventional lyophilization and subsequent reconstitution. Example 3, describes the preparation of an aqueous solution of the enzyme lactate dehydrogenase, an enzyme that loses its activity when lyophilized and then reconstituted.

EXAMPLE 3

A 1 mg/mL solution of lactate dehydrogenase (LDH) was prepared by dissolving 5 mgs LDH in 5 mL of PBS, pH 7.4. A 10 μg/mL stock solution of LDH was prepared by dissolving 200 μL of 1 mg/mL LDH solution in 19.8 mL PBS.

The gum solutions with LDH were prepared as follows: to 0.25 g of each gum or sorbitol, 2.25 mL of 10 μg/mL LDH was added and homogenized. Aliquots of 1 mL in plastic eppendorf tubes were frozen at −70° C. for 30 min and lyophilized overnight using a Labconco model 77530 lyophilizer. To each tube of the LDH lyophilizate, 2.25 mL water was added to give a reconstituted solution of 10 μg/ml enzyme. The reconstituted lactate dehydrogenase was assayed for activity using the published literature method of Lovell and Winzor (Biochemistry, 1974, v13, 3527). The results are summarized in Table 6.

TABLE 6

Stabilization of Lyophilized Lactate Dehydrogenase[a]

| Stabilizer | Concentration Before Lyophilization | % Activity Recovered |
|---|---|---|
| None | 10 | 20 |
| Sorbitol | 10 | 20 |
| Gum Arabic | 10 | 64 |
| Xanthan gum | 10 | 37 |
| Locust Bean Gum | 10 | 93 |
| Agarose | 10 | 59 |
| Guar Gum | 10 | 78 |

[a]the "% Activity" was not corrected for the extraction yield of chymotrypsin from the gum solution.

As shown in Table 6, polysaccharide gums were tested for their ability to stabilize lactate dehydrogenase, an enzyme that loses activity when lyophilized. Both the gums that were effective thermal stabilizers (i.e., gum arabic, guar gum, xanthan gum, locust bean gum) and a gum that provided no thermal stabilization (i.e., agarose) were effective stabilizers of lactate dehydrogenase during the lyophilization process. This result indicates that polysaccharide gums are effective stabilizers of a lyophilized protein and shows that the gums can be used to protect therapeutic proteins that are lyophilized prior to their addition to a drug delivery device. The protein/polysaccharide powder may be added to the delivery device dry, as a solution, or as a slurry. The lyophilized protein-polysaccharide gums powder will be useful for long term shelf storage of therapeutic proteins as well.

EXAMPLE 4

Following the procedure described in Example 1, solutions of lactate dehydrogenase (50 μg/mL) and glucose-6-phosphate dehydrogenase (50 μg/mL) were subjected to accelerated aging at respectively 60° C. and at 50° C. for 10 minutes each. The activity of lactate dehydrogenase was assayed in accordance with the procedure described in Example 3. The activity of glucose-6-phosphate dehydrogenase was assayed using the method published in Arch. Biochem. Biophys, 1998, v360, p10–14. The results are summarized in Table 7.

TABLE 7

Thermal Stabilization of Lactate Dehydrogenase and Glucose-6-Phosphate Dehydrogenase By Polysaccharide Gums

| Protein | Conc. of Protein | Stabilizer | Con. of Stabilizer (% w/v) | Accelerated Aging Conditions | % Activity |
|---|---|---|---|---|---|
| Lactate Dehydrogenase | 50 μg/mL | None | 0 | 60° C.; 10 min | 2 |
| Lactate Dehydrogenase | 50 μg/mL | Trehalose | 20 | 60° C.; 10 min | 2 |
| Lactate Dehydrogenase | 50 μg/mL | Gum Arabic | 33 | 60° C.; 10 min | 23 |
| Glucose-6-phosphate dehydrogenase | 50 μg/mL | Gum Arabic | 33 | 50° C.; 10 min | 5 |
| Glucose-6-phosphate dehydrogenase | 50 μg/mL | Guar Gum | 20 | 50° C.; 10 min | 60 |
| Glucose-6-phosphate dehydrogenase | 50 μg/mL | Trehalose | 20 | 50° C.; 10 min | 20 |
| Glucose-6-phosphate dehydrogenase | 50 μg/mL | None | 0 | 50° C.; 10 min | 0 |

Because release from the microcapsule is an essential requirement for the gums to be used for protein delivery, the release of chymotrypsin from the polysaccharide gums was evaluated. As shown in FIG. 2, chymotrypsin was dissolved in a solution containing 30% gum arabic and added to capsules that contained 100K molecular weight cut off dialysis membranes. The protein diffuses out of the viscous polysaccharide, through the membrane, and into solution at approximately 85% of the rate at which chymotrypsin diffuses from aqueous buffer through the membrane. The rates at which chymotrypsin diffuses through guar gum and locust bean gum through the membrane are approximately 20% of the rate obtained with the aqueous control. This indicates that guar and locust bean gums can be used to significantly reduce the rate of protein delivery through a membrane device, in addition to providing stabilization for the protein. Additionally, mixtures of various gums can effectively be used to stabilize and control the release of therapeutic proteins from implantable capsules.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A heat stable aqueous solution or gel comprising a biologically effective amount of a protein and a stabilizing effective amount of a polysaccharide gum material; provided that said gum material is not gum arabic at a concentration of from about 0.01 to about 10% by weight.

2. A heat stable aqueous solution or gel according to claim 1 containing one or more minor amounts of a pharmaceutically acceptable excipient.

3. A heat stable aqueous solution or gel according to claim 2 wherein said pharmaceutically acceptable excipient is selected from the group consisting of antioxidants, preservatives and surface active agents.

4. A heat stable aqueous solution or gel according to claim 1 wherein said protein comprises an enzyme, an antibody, a hormone, a growth factor, and a cytokine.

5. A heat stable aqueous solution or gel according to claim 4 wherein said protein is a hormone.

6. A heat stable aqueous solution or gel according to claim 4 wherein said protein is a cytokine.

7. A heat stable aqueous solution or gel according to claim 1 wherein said gum comprises gum arabic, guar gum, xanthan gum, locust bean gum, tragacanth gum, gum karaya, and gum ghatti.

8. A heat stable aqueous solution or gel according to claim 7 wherein said gum is present at from about 5% (W/V) to from about 33% (W/V).

9. A heat stable aqueous solution or gel according to claim 8 wherein said gum is present at from about 10% (W/V) to from about 33% (W/V).

10. A heat stable aqueous solution or gel according to claim 9 wherein said gum is present at from about 20% (W/V) to from about 33% (W/V).

11. A heat stable aqueous solution or gel according to claim 10 wherein said gum is gum arabic.

12. A heat stable aqueous solution or gel for use in an implantable drug delivery device comprising a pharmaceutically effective amount of a protein and a stabilizing effective amount of a polysaccharide gum material; provided that said gum material is not gum arabic at a concentration of from about 0.01 to about 10% by weight.

13. A heat stable solution or gel according to claim 12 wherein said stabilized solution or gel contains one or more minor amounts of a pharmaceutically acceptable excipient.

14. A heat stable aqueous solution or gel according to claim 13 wherein said pharmaceutically acceptable excipient is selected from the group consisting of antioxidants, preservatives and surface active agents.

15. A heat stable aqueous solution or gel according to claim 12 wherein said protein is selected from the group consisting of an antibody, a hormone, a growth factor, and a cytokine.

16. A heat stable aqueous solution or gel according to claim 15 wherein said protein is a hormone or a growth factor.

17. A heat stable aqueous solution or gel according to claim 15 wherein said protein is a cytokine.

18. A heat stable aqueous solution or gel according to claim 12 wherein said gum is selected from the group consisting of gum arabic, guar gum, xanthan gum, locust bean gum, tragacanth gum, gum karaya, and gum ghatti.

19. A heat stable aqueous solution or gel according to claim 18 wherein said gum is present at from about 5% (W/V) to from about 33% (W/V).

20. A heat stable aqueous solution or gel according to claim 19 wherein said gum is present at from about 10% (W/V) to from about 33% (W/V).

21. A heat stable aqueous solution or gel according to claim 20 wherein said gum is present at from about 20% (W/V) to from about 33% (W/V).

22. A heat stable aqueous solution or gel according to claim 21 wherein said gum is gum arabic.

23. An implantable drug delivery device containing a heat stable aqueous solution or gel comprising a pharmaceutically effective amount of a protein and a stabilizing effective amount of a polysaccharide gum material; provided that said gum material is not gum arabic at a concentration of from about 0.01 to about 10% by weight.

24. An implantable drug delivery device according to claim 23 wherein said stabilized solution or gel contains one or more minor amounts of a pharmaceutically acceptable excipient.

25. An implantable drug delivery device according to claim 24 wherein said pharmaceutically acceptable excipient is selected from the group consisting of antioxidants, preservatives and surface active agents.

26. An implantable drug delivery device according to claim 23 wherein said protein is selected from the group consisting of an antibody, a hormone, a growth factor, and a cytokine.

27. An implantable drug delivery device according to claim 26 wherein said protein is a hormone or a growth factor.

28. An implantable drug delivery device according to claim 23 wherein said gum is selected from the group consisting of gum arabic, guar gum, xanthan gum, locust bean gum, tragacanth gum, gum karaya, and gum ghatti.

29. An implantable drug delivery device according to claim 28 wherein said gum is present at from about 5% (W/V) to from about 33% (W/V).

30. An implantable drug delivery device according to claim 29 wherein said gum is present at from about 10% (W/V) to from about 33% (W/V).

31. An implantable drug delivery device according to claim 30 wherein said gum is present at from about 20% (W/V) to from about 33% (W/V).

32. An implantable drug delivery device according to claim 31 wherein said gum is gum arabic.

\* \* \* \* \*